United States Patent [19]

Gainer, Jr.

[11] 4,009,270
[45] Feb. 22, 1977

[54] METHOD FOR TREATING SPINAL CORD INJURY

[75] Inventor: James V. Gainer, Jr., Kingwood, W. Va.

[73] Assignee: The University of Virginia, Charlottesville, Va.

[22] Filed: Nov. 21, 1975

[21] Appl. No.: 634,149

[52] U.S. Cl. .............................. 424/195; 424/180; 424/314; 424/318; 424/325; 424/343
[51] Int. Cl.² ................ A61K 35/78; A61K 31/70; A61K 31/045
[58] Field of Search .......... 424/180, 314, 318, 325, 424/343, 195

[56] References Cited

UNITED STATES PATENTS 3,788,468  1/1974  Gainer .............................. 210/59

Primary Examiner—Sam Rosen
Attorney, Agent, or Firm—Oblon, Fisher, Spivak, McClelland & Maier

[57] ABSTRACT

A method for the treatment of spinal cord injuries in a mammal which comprises administering to said stricken mammal an effective dose of a water soluble carotenoid, or prophylactically treating a mammal which is expected to undergo spinal cord injury, such as prior to surgical procedures in the vicinity or on the spinal cord, which comprises administering to said mammal an effective dose of a water soluble carotenoid.

5 Claims, 1 Drawing Figure

METHOD FOR TREATING SPINAL CORD INJURY

BACKGROUND OF THE INVENTION

1. Field of the Invention

This invention relates to a novel technique for the treatment of spinal cord injuries in mammals.

2. Description of the Prior Art

In U.S. Pat. Nos. 3,853,993 and 3,788,468, it is disclosed that certain water-soluble carotenoids had been observed to possess quite unique properties. In particular, these water-soluble carotenoids have been found to increase the diffusivity of oxygen through aqueous media. The effect was found further to be useful biologically in the treatment of atherosclerosis, which had been theorized as being a disease resulting from local hypoxia of the vascular walls.

The study of the biological effects of this compound had continued with the discovery that it is also effective in the treatment of cerebral edema (U.S. patent application filed concurrently herewith).

It has now been found that the water soluble carotenoids are quite effective in the treatment of spinal cord injuries.

Spinal cord injury is a condition characterized by contusion of the neural tissue with resultant decrease or loss of its ability to function properly and transmit nerve impulses. The usual cause is due to an impact injury of some nature, but it may also occur during the manipulation attendant to certain surgical procedures. The early changes which occur are hemorrhagic and ischemic lesions which appear in central portions (gray matter) of the spinal cord. Initially, the periphery of the cord will show only occasional small hemorrhages in the usual case. With time the white matter in the periphery of the spinal cord will develop progressive edema, leading eventually to necrosis of this area.

The initial loss of central gray matter can be tolerated by man and most animals, since the resultant neurologic deficit is not great. However, with white matter loss in the periphery of the cord, the distal functioning fibers and neurons are rendered useless. And, with a segmental loss of white matter paraplegia or quadriplegia occurs.

The edema and necrosis in the white matter has a temporal separation of perhaps a few hours from the time of injury. Obviously then any therapeutic modality which would prevent these changes from occurring would be of great benefit in the treatment of these injuries and in the attenuation of paralysis resulting from them. At the present time no satisfactory treatment has been devised for this condition.

A number of investigators in recent years have demonstrated that the sequential pathologic changes following spinal cord injury involve alterations of vascular dynamics and progressive ischemia. The edema and necrosis which follow have been considered to be secondary changes, resulting from ischemia. Experimentally, certain modalities of therapy which have involved providing a relative increase in available oxygen have been shown to be of benefit. Hyperbaric oxygenation was studied by Kelly, DL Jr., Lassiter, KRL, Vongsvivut, A, Smith, JM: Effects of hyperbaric oxygenation and tissue oxygen studies in experimental paraplegia. J. Neurosurg. 36:425–429, 1972 and shown to be beneficial. Hypothermia by means of localized spinal cord cooling has been effective in various studies. By this method, a decrease in cellular metabolic needs would result in a decreased oxygen need. Dexamethasone has heretofor been shown to improve the functional result: Black, P. Markowitz, RA: Experimental spinal cord injury in monkeys: comparison of steroids and local hypothermia. Surg Forum. 22:409–411, 1971.

The reason why dexamethasone is effective for this purpose however, has never been clearly understood. It was believed that this compound had some effect in altering the permeability of certain tissues in the vicinity of the injury through which fluids could be passed.

DETAILED DESCRIPTION OF THE PREFERRED EMBODIMENTS

Figure 1:
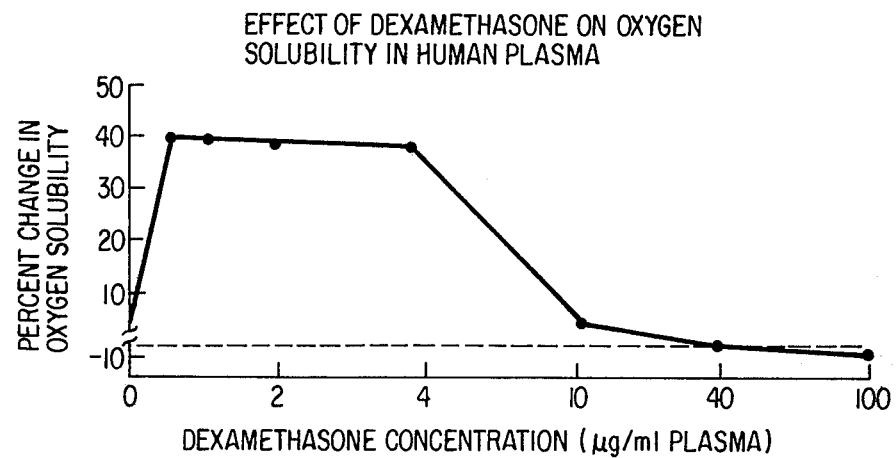

The present inventor began his study of spinal cord injuries with an investigation of the mechanism to explain the effectiveness of dexamethasone, which was formerly used for the treatment.

The studies of the present inventor have determined that dexamethasone concentrations of 0.5–4.0 micrograms/millilitter increase the solubility of oxygen in plasma by about 40% (FIG. 1). Each of these therapeutic modalities then has the effect of providing a relative increase of available oxygen at the level of the capillary endothelial cell.

This net increase in oxygen at this level may be a means of providing free radical scavenging and/or in maintaining mitochondrical function.

The water soluble carotenoids have been shown to produce an increase in the diffusion speed (diffusivity) of oxygen through plasma of approximately 80%. (U.S. Pat. Nos. of 3,788,468 and 3,853,993) When dissolved in plasma, the compounds cause an increase in diffusivity of oxygen, carbon dioxide, and various other compounds.

Since utilization of these compounds should produce a net increase in available oxygen at the capillary endothelial level, it seemed that it might have some efficacy in the therapy of spinal cord injury.

This theory was tested and determined to be correct by empirical investigation.

The carotenoids useful for this purpose are those of the form:

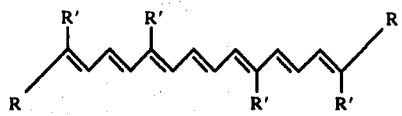

wherein each R may represent a hydrophilic group and each R' represents hydrogen or methyl. Suitable hydrophilic groups include the carboxyl groups or the ester groups of the form COOR "wherein R' represents a soluble sugar group, such as $C_{12}H_{21}O_{10}$, an alkanol group, such as —$CH_2$—OH, —$CH_2$—$CH_2$OH, or —$CH_2$—$CH_2$—OH, or a carboxy substituted lower alkyl, such as —$CH_2$—COOH, —$CH_2$—$CH_2$COOH or —$CH_2$—$CH_2$—COOH, or each R and R' may represent a lower alkanol group, such as —$CH_2$—OH, —$CH_2$—$CH_2$—OH, or —$CH_2$—$CH_2$—$CH_2$—OH, a hydroxy group, or an amine group of the form — NH or NR''' wherein R''' is a lower alkyl, lower alkanol or carboxy substituted lower alkyl, or a carboxy substituted lower alkyl, such as —$CH_2$—$CH_2$—OH, —$CH_2$—OH or $CH_2$—$CH_2$—$CH_2$—OH.

Most preferred are crocetin, also known as 8,8'-diapo-8,8'-carotenedioate, or a salt, such as the sodium salt, of crocetin.

The water soluble carotenoids have been found to be effective in the treatment of spinal cord injuries when applied either by injection intramuscularly, or intravenously into the animal. They could also be given orally.

The carotenoid can be injected into the patient, and in an injectable form, it may be combined with vitamins, choline, glycerophosphoric acid, glycol, glycerine or gum tragacanth, etc.

The animal or human is treated with from 0.001 to 1000 mg of active ingredient per kg of body weight each application, for a total weekly dose rate of 0.001 to 1000 mg of active ingredient per kg of body weight/day, and preferably, from 0.005 to 500 mg/kg/day or 0.001 to 1000 mg/kg/week.

The effectiveness of the water soluble carotenoids has been indicated by tests with mongrel dogs, which are standard test animals often used for experimental treatment techniques of this disorder.

Having generally described the invention, a more complete understanding can be obtained by reference to certain specific examples, which are included for purposes of illustration only and are not intended to be limiting unless otherwise specified.

EXAMPLES

Mongrel dogs of both sexes weighing 15–30 kg. were anesthetized with pentobarbital. The pentobarbital dosage was 30 mg/kg and was given as a single intravenous bolus. The animals were intubated and maintained with a Harvard Respiration Pump on room air. They were placed on the operating table in the prone position, and the mid-back area was prepped and draped as a sterile field. Using aseptic technique a total laminectomy of $T_9$ or $T_{10}$ was done. A single level laminectomy was utilized in the large majority of cases. A 20 Gm. weight was then dropped on the cord through a cylindrical tube for a distance of 25 cm. The injury was delivered to the cord with the dura intact. The wound was then closed in layers with 3–0 silk suture. The animals were maintained in the vivarium for a period of four weeks, and their neurologic function assessed weekly.

The treatment schedules for the animals were as follows:
1. Control Group
   No treatment.
2. Pre-treated Group Crocetin was given in a dose of 45 micrograms/kg. intravenously once daily for two days prior to the lesion, 45 micrograms/kg three times daily on the day of surgery and then 45 micrograms/kg. twice daily after the lesion. After the surgery, two-thirds of the dose was given intravenously and one-third intramuscularly. The treatment was continued for twelve days.

3. Post-treated Group

Crocetin was given in a dose of 90 micrograms/kg. twice daily beginning 30 minutes after the lesion, and continuing for twelve days. Two-thirds of the dose was given intravenously and one-third intramuscularly.

The dogs were assessed at the end of each week and graded by the system proposed by Tarlov.

The animals were graded weekly using the Tarlov classification, i.e., 0 = no movement of legs; 1 = minimal leg movements; 2 = good leg movements; 3 = able to stand and possibly walk: 4 = able to walk and run with minimal or no deficit. The results are presented in Table 1.

Table I.

|  | First Week | Second Week | Third Week | Fourth Week |
|---|---|---|---|---|
| CONTROL |  |  |  |  |
| 1. | 0 | 0 | 0 | 0 |
| 2. | 0 | 1 | 1 | 2 |
| 3. | 0 | 0 | 0 | 1 |
| 4. | 0 | 0 | 1 | 2 |
| 5. | 0 | 0 | 0 | 0 |
| 6. | 0 | 0 | 1 | 1 |
| PRE-TREATED |  |  |  |  |
| 1. | 2 | 3 | 4 | 4 |
| 2. | 1 | 2 | 2 | 2 |
| 3. | 2 | 3 | 3 | 4 |
| 4. | 2 | 2 | 3 | 3 |
| 5. | 1 | 1 | 2 | 2 |
| POST-TREATED |  |  |  |  |
| 1. | 1 | 2 | 3 | 4 |
| 2. | 1 | 1 | 2 | 3 |
| 3. | 1 | 2 | 3 | 3 |
| 4. | 2 | 3 | 3 | 3 |

Comparison of the control animals with both the pre-treated and post-treated groups gave a significance level of .05 or better.

Each week the crocetin treated dogs were significantly improved over the control group. This was true for both pre-treated and post-treated animals. No significant difference was apparent between the pre-treated and post-treated groups. While this represents a small number of animals, it was of sufficient size to be statistically significant in that all comparisons differed at the .05 level or better. The animals manifested no signs of untoward reactions to the crocetin which was administered. They did have the usual problems associated with spinal cord injury of urinary retention and decubitus ulcerations.

There is some evidence that the early pathophysiologic change which occurs in a traumatized but intact spinal cord is that of local ischemia. This occurs in the first few hours and results in secondary necrosis which is irreversible. In this study it was attempted to determine if an increase in the rate of plasma oxygen diffusion would have any effect in counteracting this hypoxia, and reduce the secondary necrosis of neural tissue. The results of this study were very encouraging, and indicate that this may be a new avenue of approach to the treatment of spinal cord injury.

The primary effect of the water-soluble carotenoids is to increase the diffusivity of oxygen through the plasma. In all probability it increases the diffusivity of other compounds in plasma too, and may hasten the removal of lactic acid, for example.

The combination of intravenous and intramuscular dosage seem to produce a diffusivity increase lasting several hours. One of the dogs tested was pregnant and her puppies showed no evidence of congenital abnormalities.

Having now fully described the invention, it will be apparent to one of ordinary skill in the art that many changes and modifications can be made thereto without departing from the spirit or scope of the invention as set forth herein.

What is claimed as new and intended to be covered by letters patent is

1. A method for the treatment of spinal cord injuries comprises administering to a host inflicted with injury or expected to be inflicted with injury resulting in a traumatized, ischemic spinal cord, an effective dose of a water-soluble carotenoid sufficient to reduce secondary necrosis of neural tissue.

2. The method of claim 1, wherein said water-soluble carotenoid has the formula

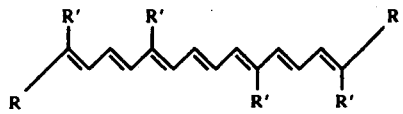

wherein each R is a hydrophilic group, and wherein each R' is hydrogen or methyl.

3. The method of claim 1, wherein said water-soluble carotenoid is crocin.

4. The method of claim 1, wherein said water-soluble carotenoid is crocetin.

5. The method of claim 1, wherein said water-soluble carotenoid is administered intravenously or intramuscularly at a dose rate of from 0.001 mg to 1000 mg active ingredient per kg of body weight per week.

* * * * *